(12) United States Patent
Ward et al.

(10) Patent No.: US 8,079,955 B2
(45) Date of Patent: Dec. 20, 2011

(54) METHOD AND APPARATUS FOR MANAGING GLUCOSE CONTROL

(75) Inventors: W. Kenneth Ward, Portland, OR (US); Richard Sass, Portland, OR (US); Robert Bruce, Portland, OR (US)

(73) Assignee: iSense Corporation, Wilsonville, OR (US)

( * ) Notice: Subject to any disclaimer, the term of this patent is extended or adjusted under 35 U.S.C. 154(b) by 1250 days.

(21) Appl. No.: 11/689,745

(22) Filed: Mar. 22, 2007

(65) Prior Publication Data

US 2008/0125636 A1 May 29, 2008

Related U.S. Application Data

(60) Provisional application No. 60/867,507, filed on Nov. 28, 2006.

(51) Int. Cl.
*A61N 5/00* (2006.01)

(52) U.S. Cl. .................................. 600/365; 600/347

(58) Field of Classification Search .................. 600/365, 600/319, 347
See application file for complete search history.

(56) References Cited

U.S. PATENT DOCUMENTS

| 5,822,715 | A | 10/1998 | Worthington et al. |
| 6,175,752 | B1 | 1/2001 | Say et al. |
| 6,233,471 | B1 | 5/2001 | Berner et al. |
| 6,294,062 | B1 * | 9/2001 | Buck et al. ................. 204/400 |
| 6,572,542 | B1 | 6/2003 | Houben et al. |
| 6,585,644 | B2 * | 7/2003 | Lebel et al. ................. 600/300 |
| 7,022,072 | B2 * | 4/2006 | Fox et al. ...................... 600/365 |
| 2003/0060765 | A1 * | 3/2003 | Campbell et al. ............ 604/131 |
| 2005/0059895 | A1 * | 3/2005 | Brown ........................ 600/481 |
| 2006/0094947 | A1 | 5/2006 | Kovatchev et al. |
| 2008/0133146 | A1 | 6/2008 | Chang et al. |

* cited by examiner

*Primary Examiner* — Charles A Marmor, II
*Assistant Examiner* — Tho Tran
(74) *Attorney, Agent, or Firm* — Schwabe, Williamson & Wyatt, P.C.

(57) ABSTRACT

Embodiments of the present invention provide methods, apparatuses, and systems associated with detecting, analyzing, and/or displaying historical glucose levels and/or trends in a body.

18 Claims, 3 Drawing Sheets

Example of Glucose Data and Method of
Calculating a Glucose Control Index

FIG. 3
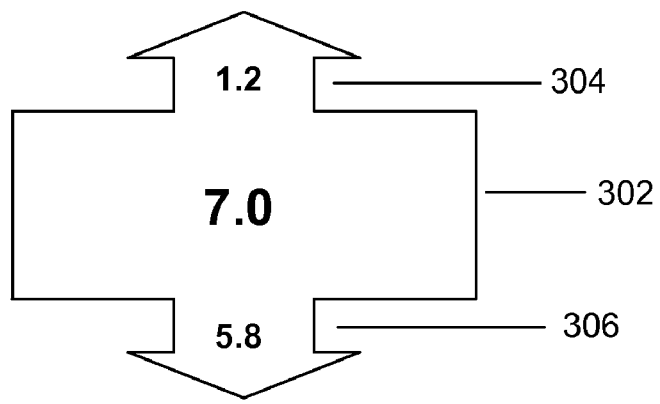
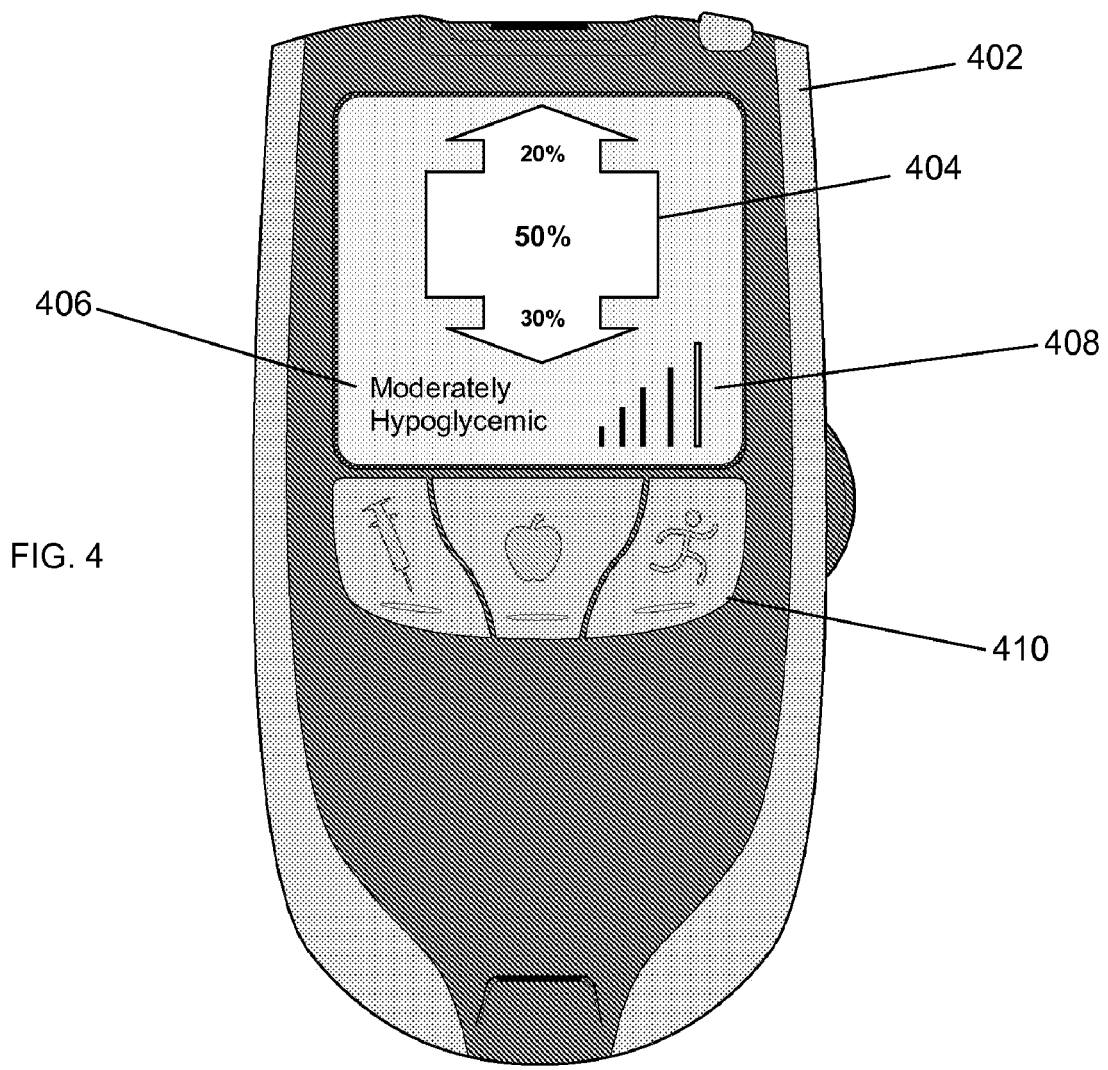
FIG. 4

METHOD AND APPARATUS FOR MANAGING GLUCOSE CONTROL

CROSS REFERENCE TO RELATED APPLICATIONS

The present application claims priority to U.S. patent application No. 60/867,507, filed Nov. 28, 2006, entitled "Method and Apparatus for Managing Glucose Control," the entire disclosure of which is hereby incorporated by reference in its entirety.

TECHNICAL FIELD

Embodiments of the invention relate generally to the field of medical devices and, specifically, to methods, apparatuses, and systems associated with detecting, analyzing, and/or displaying historical glucose levels and/or trends in a body.

BACKGROUND

In persons with diabetes who take insulin or oral agents, hypoglycemia (low blood sugar) may be a serious event. In some situations, hypoglycemia may lead to loss of cognitive abilities, seizures, stupor or coma. The range of ill effects from hypoglycemia range from embarrassment (losing one's train of thought in a meeting) to more serious outcomes such as auto accidents. For these reasons, detection of hypoglycemia is one of the most important benefits of continuous glucose sensing. Hyperglycemia (elevated blood sugar) may cause problems as well, such as damage to nerves, blood vessels, and organs, and may lead to further serious conditions such as ketoacidosis or hyperosmolar syndrome.

Thus, it would be useful to provide a user with simple and effective mechanisms to monitor the user's historical glucose values to provide information about trends to aid in the user's management and control of glucose levels.

BRIEF DESCRIPTION OF THE DRAWINGS

Embodiments of the present invention will be readily understood by the following detailed description in conjunction with the accompanying drawings. Embodiments of the invention are illustrated by way of example and not by way of limitation in the figures of the accompanying drawings.

FIG. 3 illustrates a graphical and numeric representation of a glucose control index and exemplary associated values in accordance with various embodiments of the present invention;

FIG. 4 illustrates an exemplary electronic monitoring unit showing various display features in accordance with various embodiments of the present invention.

DETAILED DESCRIPTION OF EMBODIMENTS OF THE INVENTION

Figure 1:
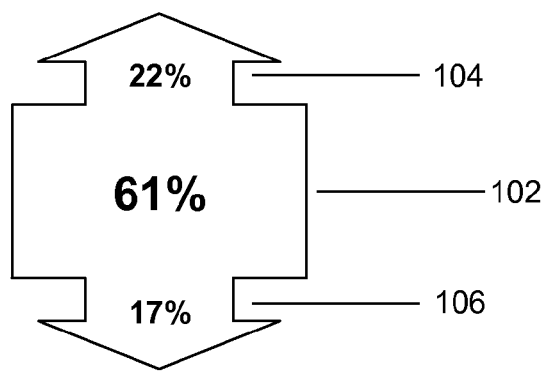
FIG. 1 illustrates a graphical and numeric representation of a glucose control index and exemplary associated values in accordance with various embodiments of the present invention.

In the following detailed description, reference is made to the accompanying drawings which form a part hereof, and in which are shown by way of illustration embodiments in which the invention may be practiced. It is to be understood that other embodiments may be utilized and structural or logical changes may be made without departing from the scope of the present invention. Therefore, the following detailed description is not to be taken in a limiting sense, and the scope of embodiments in accordance with the present invention is defined by the appended claims and their equivalents.

Various operations may be described as multiple discrete operations in turn, in a manner that may be helpful in understanding embodiments of the present invention; however, the order of description should not be construed to imply that these operations are order dependent.

The description may use perspective-based descriptions such as up/down, back/front, and top/bottom. Such descriptions are merely used to facilitate the discussion and are not intended to restrict the application of embodiments of the present invention.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" means A or B. For the purposes of the description, a phrase in the form "A and/or B" means "(A), (B), or (A and B)". For the purposes of the description, a phrase in the form "at least one of A, B, and C" means "(A), (B), (C), (A and B), (A and C), (B and C), or (A, B and C)". For the purposes of the description, a phrase in the form "(A)B" means "(B) or (AB)" that is, A is an optional element.

The description may use the phrases "in an embodiment," or "in embodiments," which may each refer to one or more of the same or different embodiments. Furthermore, the terms "comprising," "including," "having," and the like, as used with respect to embodiments of the present invention, are synonymous.

In various embodiments of the present invention, methods, apparatuses, and systems for detecting, analyzing, and/or displaying historical glucose levels and/or trends in a body are provided. In exemplary embodiments of the present invention, a computing system may be endowed with one or more components of the disclosed apparatuses and/or systems and may be employed to perform one or more methods as disclosed herein.

Embodiments of the present invention provide methods, apparatuses, and systems associated with detecting, analyzing, and/or displaying historical glucose levels and/or trends in a body. Embodiments of the present invention provide glucose control indices and methods for monitoring and/or displaying glucose control characteristics.

In an embodiment, there is provided a method, comprising measuring with a glucose sensing device a plurality of glucose values of an individual for a plurality of points of time over a defined time period; determining for the plurality of points of time over the defined time period the relative integrated percentages of hyperglycemia, hypoglycemia, and normoglycemia; identifying a glucose level condition of the individual based on the relative integrated percentages of hyperglycemia, hypoglycemia, and normoglycemia; and providing a notification of the glucose level condition to the individual.

In an embodiment, the term "integrated percentage" refers to the area between a curve and a line and is indicative of the magnitude and extent of the difference(s) between the line and the curve expressed as a percent area of the total area encompassed over a period of time.

In an embodiment, the term "integrated percentage" may include a simplified mathematical approach in which each region is defined as the sum of the differences between the nearest boundary value and the actual value for each included point of time (for example each measured minute, etc.). Thus, if the region of interest contains four minutes in which measurements were taken (minutes 1, 2, 3, and 4), the nearest boundary was 180, and the respective measured values were 185, 187, 187, 189, then the resulting integrated percentage would be 5+7+7+9=28.

In an embodiment, the term "glucose level condition" comprises a current and/or historical status of the glucose level of an individual, and may, in an embodiment, be displayed in textual form (stating the current status with indicators such as "moderately hypoglycemic" or "125 mg/dl" etc.) or graphical form (showing boxes, arrows, etc. in conjunction with or separate from numeric values).

In an embodiment, multiple measurements may be viewed or utilized in combination to provide an indication of the success of control measures taken by an individual. In an embodiment, one or more values may be used to determine an individual's success at controlling glucose levels in his/her body, and may further be used to provide information or recommendations to ensure better control in the future. In embodiments, such values may include (1) the average glucose level (may be provided from A1C and/or average sensed values), (2) the deviation of glucose values (for example, the coefficient of variation or the standard deviation—may come from the continuously sensed values), and (3) the number and severity of hypoglycemia and/or hyperglycemia spells (the degree and duration of hypoglycemia and/or hyperglycemia).

In embodiments, the one or more metrics used to evaluate an individual's glucose level control may be weighted equally or differently as desired.

The hemoglobin A1C has been a valuable tool for persons with diabetes. It provides an average of glucose values over a measured period, such as a 2-3 month period. For example, if a person's A1C value is 14%, then he/she knows that their average level of glycemia is extremely high. Typically this would mean that more insulin, more exercise, or less ingested carbohydrate (or some combination of the three) would be recommended.

If a person's A1C is 6%, then the situation is very different. Such a value may be present in many different situations, two of which are highlighted below for exemplary purposes.

In the first example of an individual in which A1C=6%, the glucose values are well-controlled and are almost all between 75 mg/dl and 150 mg/dl. In such a case, the short term and long term outlook are both very good if such a degree of control is continued.

In a second example of an individual in which A1C=6%, the glucose values are quite variable and vary from 35 mg/dl (dangerously low) to 250 mg/dl (quite high). Such an individual may be at high risk for stupor, coma, seizures, automobile accidents, and sudden death from severe hypoglycemia (and/or potentially hyperglycemia) but may have little indication from the A1C value.

With the advent of continuous glucose monitoring (CGM), it is possible to provide an index that is much more informative than the A1C. In an embodiment, such an index of glucose control may have three parts, a normoglycemia value, a hypoglycemia value, and a hyperglycemia value. The determination of which glucose values fall within which classification may be made by one of ordinary skill in the art in light of the teachings herein and in conjunction with the knowledge in the art.

In an embodiment, the values described above may be displayed. A normoglycemia number (for example centrally displayed and/or in a larger font) is the area (glucose values over time providing an integrated percentage) within the normal range (lower than the hyperglycemia boundary and higher than the hypoglycemia boundary). In an embodiment, a hyperglycemia number is the area at or above the hyperglycemia boundary and the hypoglycemia number is the area at or below the hypoglycemia boundary. In an embodiment, the numbers may be displayed, for example, as shown in FIG. 1, with the normoglycemia number shown in 102, the hyperglycemia number shown in 104, and the hypoglycemia number shown in 106.

In an embodiment, the upper (hyperglycemia) and lower (hypoglycemia) numbers 104, 106 may be in a smaller font from that of the normoglycemia number 102. In an alternative embodiment, the font size may be variable and may match with the value of the raw numbers. In other words, in an embodiment, a large hypoglycemia value may be displayed with a large font. In embodiments, one or more of the numbers or portions of the display may be color coded. For example, in an embodiment, the normoglycemia region may be displayed in green, the hypoglycemia region in red, and the hyperglycemia region in blue or yellow. In an embodiment, the colors may be dynamic and change with the values being displayed to provide further emphasis. In addition, as shown in FIG. 1, the upper and lower regions may be shown with arrows, or some other graphical symbol. In embodiments, the length and/or width of the arrows (as well as the size of the central normoglycemia region) may be dynamic and may correspond to the relative percentages/magnitudes of each region.

In an embodiment, the percentages for each region indicate the percent area of the total area for the selected duration. Thus, in such an embodiment, all three values add up to a total of 100%.

In embodiments, a glucose control index may be provided over any duration, from a few hours up to many weeks or months. Note, for example, that if a person is concerned about the hours between 1 AM and 6 AM, then he/she may calculate his/her glucose control index over that time period for one night only or over many nights. Thus, for example, an index may be determined for a continuous time period of 4 weeks, or an index may be determined for the time period of 1 AM to 6 AM for a period of 4 weeks, etc.

In an embodiment, assume the upper boundary is 180 mg/dl and the lower boundary is 70 mg/dl (the upper/lower boundaries refer to the boundaries of the normoglycemia area, and, in embodiments, may or may not include one or both end points of the region). In the case of an individual whose control is good, the individual might have an upper value of 9%, a middle value of 90%, and a lower value of 1%. In an embodiment, such values may be abbreviated as 9/90/1. This would indicate that the individual rarely has low values and only occasionally has high values. In embodiments, the boundaries may be set as desired by an individual or health professional.

In an embodiment, assume an individual has an upper value of 30%, a middle value of 50%, and a lower value of 20%, abbreviated, for example, as 30/50/20. Thus, the individual has frequent hypoglycemia and frequent hyperglycemia and may be at risk for serious consequences of hypoglycemia. The individual is probably not at risk for long term complications, however, since the individual's average glucose is good and the average glucose is the primary determinant of long term disease of the retina, kidney, nerves and cardiovascular system.

It is important to note that the index values as described above indicate areas, not percentages of time in given regions. To illustrate this concept, assume a hypoglycemia cutoff/boundary of 70 mg/dl, and assume that 4 values are obtained (once per minute) for the purpose of comparison. In the case of a first individual, the values are each 60 mg/dl. Therefore the area below the cutoff is 10 mg/dl×4 minutes, yielding an area of 40. In the case of a second individual, the values are each 40 mg/dl, yielding a comparable area of 120. Thus, in this comparison, although the individuals have the same number of minutes below the cutoff, the latter has a greater clinical danger, and so his/her lower (hypoglycemia) number has a larger magnitude, everything else being equal.

In an embodiment, one may use the trend of the glucose control index over time. Assume that in January, an individual has a glucose control index value of 20/70/10 (upper/middle/lower). The individual and his physician then determine that the upper and lower values are too great and institute a system of carbohydrate counting, whereby the individual carefully matches his insulin to his carbohydrate intake. By March, his glucose control index value is 15/80/5 and by June, his glucose control index value is 10/86/4. This trend would indicate a steady improvement in his control. In an embodiment, this information (i.e., these trends) may be stored in a glucose monitoring unit or in another associated storage medium for later comparison, analysis, and/or display.

In a further example, assume that an individual wants to achieve even better glucose level control. The individual and his physician decide to break down the glucose control index value over different parts of the day. They examine the glucose control index for the exemplary periods 0601-1200, 1201-1800, 1801-2400, and 2401-0600.

Over an exemplary 4 week period, the following results are obtained:

| TIME | Glucose Control Index |
|---|---|
| 0601-1200 | 12/87/1 |
| 1201-1800 | 10/86/4 |
| 1801-2400 | 10/86/4 |
| 0001-0600 | 8/85/7 |
| OVERALL: | 10/86/4 |

These results indicate that the individual is relatively well-controlled from 0601-1200, with some hyperglycemia, but little hypoglycemia. From 1201-2400, the individual's glucose control index is the same as his overall value, indicating good control. However, in the very early hours of the morning (0001-0600), he experiences a rise in the lower value, indicating nocturnal hypoglycemia. In an embodiment, he may then, for example, institute a program in which he reduces his long acting insulin at bedtime and starts having a bedtime snack. One month later, his 0001-0600 glucose control index value may be, for example, 10/87/5, which is improved and now nearly the same as his overall glucose control index value. The specific time periods measured may be selected by a user, and may be in periods of minutes, hours, days, weeks and/or months, and may, in an embodiment, be unequal in duration across a series of measured time periods.

An embodiment of the present invention may be provided to incorporate goal setting into a device and/or method. For example, in an embodiment, a device may be provided in which a particular goal for the glucose control index may be established by the individual and/or a physician and set in the device. In an embodiment, there may then be visual and/or audible indicators of how the individual is doing as compared to the goal that was established. Thus, in an embodiment, an exemplary goal may be set to reduce the individual's hypoglycemia values by 5% over a one-month period, and a display may be provided that shows, for example, after two weeks that the values have dropped by 3% indicating the individual is on track to achieve the goal.

Figure 2:
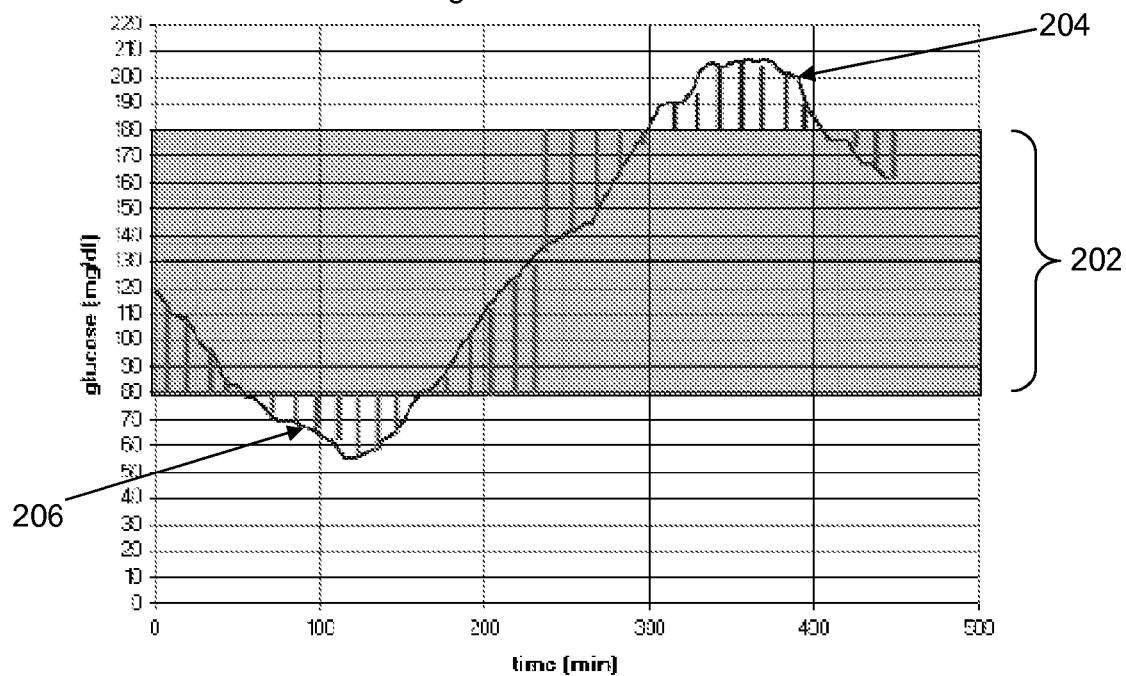
FIG. 2 illustrates a graphical plot and exemplary representation of glucose data for calculation of a glucose control index in accordance with various embodiments of the present invention.

In FIG. 2, illustrating the concept of integrated areas in accordance with an embodiment of the present invention, the uppermost hatched bars indicate hyperglycemia area 204, the central bars indicate normoglycemia area 202 and the lowermost bars indicate hypoglycemia area 206. In embodiments, the specific calculations of a glucose control index may be made by using integration or more simple mathematical estimates in order to measure the areas in each region and then express the values for each region as a percent of the total, so that all three values add to 100%. One value of using a percentage is that almost everyone is familiar with using percentages. However, there may be other methods of expressing the values. For example, in other embodiments, the time duration in each region may be used, rather than the areas.

FIG. 3 illustrates a graphical display of a glucose index control value 302 which is a sum of the index values for the hyperglycemia region 304 and the hypoglycemia region 306. Unlike the above embodiments (see FIG. 1), the present embodiment does not show a normoglycemia value. Instead, this simplified representation shows the duration of time or area (mg/dl×time) outside a defined normoglycemia region. The values indicate relative concerns for hypoglycemia and hyperglycemia, and, in addition, provide an overall indication of how well the individual's glucose values are being managed.

In an embodiment, the upper (hyperglycemia) and lower (hypoglycemia) numbers 304, 306 may be in a smaller font from that of the overall glucose control index value 302. In embodiments, one or more of the numbers or portions of the display may be color coded. For example, in an embodiment, the hypoglycemia region may be shown in red and the hyperglycemia region in blue or yellow. In addition, as shown in FIG. 3, the upper and lower regions may be shown with arrows, or some other graphical symbol. In embodiments, the length and/or width of the arrows may correspond to the relative percentages/magnitudes of each region.

Over time, it may be possible that health agencies or professional standards agencies may set standards or goals for the glucose control index, just as are currently in place for A1C values. Regardless of standards being established, an individual with or without the aid of a health professional may use the glucose control index values as benchmarks to strive for in managing glucose levels.

Additional measurements or metrics of glucose level control may be utilized as mentioned above, solely or in combination with other metrics. In an embodiment, a real-time glucose average may be provided. Unlike the A1C whose value comes from a measurement of hemoglobin, a real-time glucose average comes from the averaging in real-time of all the sensor values collected (such as 1440 data points per day (one per minute) in one embodiment) over however many days the glucose sensor has been worn (for example, 3, 5, 7, 14, 30, 60, 90, or more days). In an embodiment, a real-time glucose average may be calculated from glucose as contained within interstitial fluid as collected from subcutaneous tissue. In an embodiment, the real-time glucose average value may be a similar number to the A1C, and as such the user may correlate the real-time glucose average value to his/her A1C value. In an embodiment, the A1C value may serve as a starting point and the combination of the real-time glucose average and the next A1C value may provide a benchmark for an individual to manage his/her glucose values. In an embodiment, the real-time glucose average value may be recalculated from the current time backward (for whatever defined period is desired and every time the user uses that feature) to arrive at a shifting real-time average. In an embodiment, a glucose average may be calculated from a plurality of glucose values, and the values may, in an embodiment, be weighted. In an embodiment, the most recently measured glucose value may be weighted more heavily than a more distant glucose value.

Thus, in an embodiment, the real-time glucose average may be reported as a metric that correlates to an A1C value and as such calculates and provides an average of all the data points per day over the number of days the person with diabetes wears the device. In an embodiment, an A1C value may be derived from a real-time glucose average, and, in an embodiment, a real-time glucose average may be derived from an A1C value.

In an embodiment, a device may have the ability to receive and/or obtain both an A1C value and a real-time glucose average (both, for example, over the same or similar time period). Thus, in an embodiment, the derivation calculations may be used to perform a "cross-check" of the values and to verify the validity of the measurements. In an embodiment, a device may be provided with at least two integrated ports, one for obtaining an A1C value and one for obtaining a real-time glucose value, for example using a standard test strip. In an alternative embodiment, a device may allow for the physical entry of data indicative of the A1C value and/or the current glucose value having been measured using a separate device.

One concern with the use of an A1C measurement as an estimate of average glucose values is that it sometimes gives erroneous results. As an example, assume that two men both have type 1 diabetes, both are 30 years old without other medical problems, and both have exactly the same blood glucose profile. Over the prior 90 days, the glucose average of each is 150 mg/dl.

However, because of hereditary differences in the speed with which they glycate hemoglobin, one could have an A1C of 6.5% and the other could have an A1C of 7.5%. This inherited difference in glycation has been termed the "glycation gap" and can cause difficulties in the way in which patients or their health professionals assess the degree of their glycemic control (see Cohen, R M et al., Evidence for independent heritability of the glycation gap fraction of HbA1c in nondiabetic twins, Diabetes Care, Aug. 2006, 29(8):1739-43).

As an alternative to the A1C, in an embodiment, one may compute a glucose average that is based on multiple continuous glucose sensor measurements that are obtained every minute. Such a glucose average is unrelated to the glycation of hemoglobin or any other protein. For this reason, it is a better (more true) measure of average glycemia. It is also likely to be a better indicator of long term risk of diabetes complications, since it is not perturbed by vagaries of protein glycation.

In an embodiment, one or more metrics may be utilized to form a "toolbox" for the management and control of an individual's glucose levels. In embodiments, such metrics may include (1) A1C, discrete blood glucose test strip values, continuous glucose monitor values, including a discrete continuous glucose monitor snap-shot in time of a single glucose value from the continuous glucose monitor, 2) a graphical representation of glucose values over time, 3) a glucose control index value, and 4) a real-time average which is a real-time average over the duration the individual has worn a continuous glucose monitoring device (for example, a 7 day average, or a 90 day average, etc.), or a subset of such a duration. In an embodiment, a display of various metrics mentioned above may be provided, for example showing the person's excursions next to an average, next to the percentage the individual was in the various normoglycemia, hypoglycemia and hyperglycemia regions, next to a discrete glucose value with an arrow showing the slope up or down (or some other graphical representation of the trends).

Embodiments of the present invention may be utilized with a variety of known and later developed glucose sensors or monitors. For example, in an embodiment, the glucose sensor may be a small diameter wire-based device that may be inserted under the skin for 3-7 days. In another embodiment, a suitable sensor may be provided in a device that is fully implantable under the skin and that may remain inserted for 3-12 months. The biosensor(s) may be coupled in various ways to implantable or on-skin electrical components and/or external monitoring units that are capable of performing various calculations and analysis and display of data. In an embodiment, the various metrics described herein may be displayed on the screen of an electronic monitoring unit that may be, for example, worn on the belt or waistband, or in a table-top unit, to which data may be sent by a wired or wireless connection. In an embodiment, the display may provide textual or numeric readouts and/or may show a simple graphical representation of the data. In an embodiment, the various metrics described herein may be displayed on the patient's personal computer or other computing device, and/or may be displayed on reports prepared by or sent to a health professional, and/or may be displayed on the health professional's computer.

In embodiments, various types of alarms or notifications may be used to indicate the current condition, especially a condition of concern, such as an audible (alarm or electronic voice prompt), visual (for example colored or flashing lights or a symbol on the display), and/or vibratory notification. In an embodiment, a notification may provide an indication of the degree of risk or the condition of concern. In an embodiment, a notification may also provide an indication or suggestion of an action to be taken as a result of the condition of concern. For example, if it is determined that there is a moderate risk of hypoglycemia developing in the tested individual, or if the data indicates a troubling hypoglycemia trend, the sensing system may provide a suggestion to eat a snack in the next 30-60 minutes. In an embodiment, these suggestions may be customized based on the specific medication, exercise, and dietary parameters of an individual. In another example, if an extreme condition of hyperglycemia is identified, there may be provided a notification to contact a health care professional to address the situation. In an embodiment, either directly from the sensing device or from a separate monitoring unit, a condition of concern may be communicated further to a medical professional as desired or as programmed into the system, whether communicated manually or automatically.

In an embodiment of the present invention as shown in FIG. 4, an exemplary electronic monitoring unit 402 provides various notification and display features. For example, in an embodiment, a graphical representation 404 of a glucose control index may be provided. In addition, or alternatively, in an embodiment, a textual description 406 of the trend may be provided. For example, a description may be provided of the relative direction/levels indicated by the data. For example, a glucose control index of 20/50/30 (hyperglycemia/normoglycemia/hypoglycemia) may be identified as "moderately hypoglycemic". Other suitable descriptors may be utilized as desired.

In embodiments, various audible or visual displays of various degrees of concern may be provided, such as a meter 408, or other lights, flashing or colored (such as a series of green, yellow, and red lights). In addition, electronic monitoring unit 402 may provide an indication of an action to be taken based on the condition or degree of concern using various recommendation buttons or lights 410, providing exemplary recommendation options of an injection, a snack (symbolized by an apple), or exercise. An additional recommendation button may, in an embodiment, provide an indication to contact a medical professional.

Figure 5A:
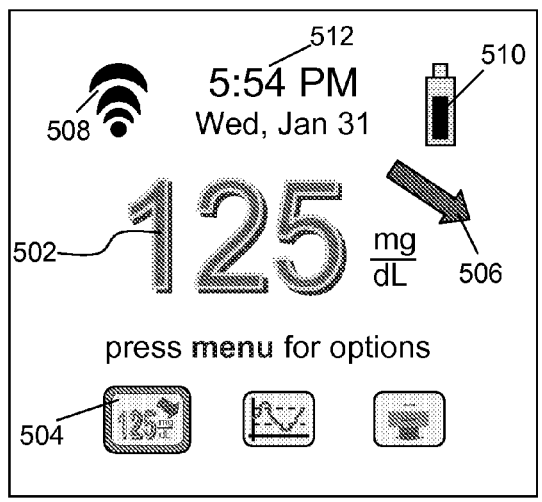
FIGS. 5A, 5B, and 5C illustrate exemplary displays for an electronic monitoring unit in accordance with an embodiment of the present invention
Figure 5B:
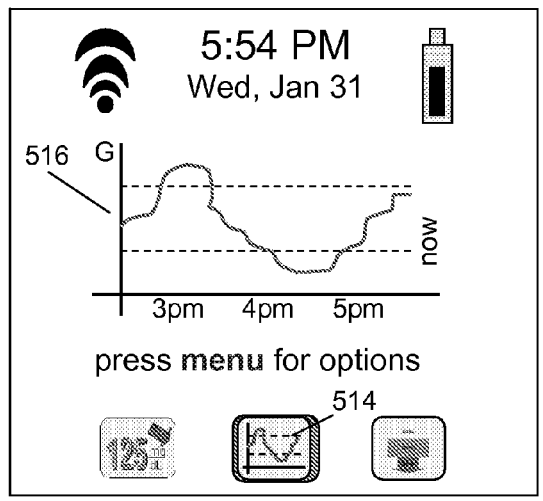
Figure 5C:
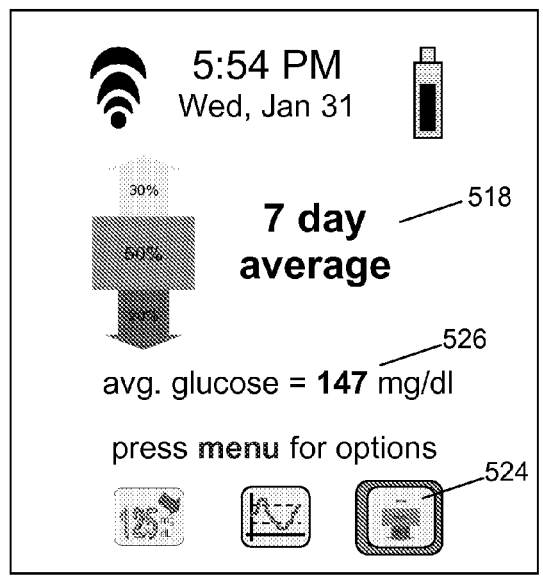

FIGS. 5A, 5B, and 5C illustrate exemplary displays for an electronic monitoring unit in accordance with an embodiment of the present invention. FIG. 5A illustrates a current glucose value 502 is being displayed in mg/dl as per the selected type of display 504 shown highlighted. Current glucose value 502 is also shown with a direction arrow 506 indicating the current glucose trend for the individual. In addition, the display includes a signal meter 508, a battery power meter 510, and a current date/time indication 512. FIG. 5B shows the change in the display when the selection of the type of display is shifted to type 514 (shown highlighted). Display type 514 provides a graphical representation 516 of the historical glucose values over a defined period of time. FIG. 5C shows the change in the display when the selection of the type of display is shifted to type 524 (shown highlighted). Display type 524 provides a combination graphical and textual representation 518 of a glucose control index, as well as an indication of the relevant time period for which the values were measured. In addition, FIG. 5C illustrates that different metrics may be combined in a single display, as a real time glucose average 526 is also provided.

Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments shown and described without departing from the scope of the present invention. Those with skill in the art will readily appreciate that embodiments in accordance with the present invention may be implemented in a very wide variety of ways. This application is intended to cover any adaptations or variations of the embodiments discussed herein. Therefore, it is manifestly intended that embodiments in accordance with the present invention be limited only by the claims and the equivalents thereof.

What is claimed is:

1. A method, comprising:
    receiving a plurality of glucose values of an individual for a plurality of points of time over a defined time period;
    determining, using an electronic monitoring unit, for the plurality of points of time over the defined time period the relative integrated percentages of hyperglycemia, hypoglycemia, and normoglycemia;
    identifying, using the electronic monitoring unit, a glucose level condition of the individual based on said relative integrated percentages of hyperglycemia, hypoglycemia, and normoglycemia; and
    providing, using the electronic monitoring unit, a notification of the identified glucose level condition, wherein said notification comprises a display of a unified graphical representation of the integrated percentages of hyperglycemia, hypoglycemia, and normoglycemia.

2. The method of claim 1, wherein said defined time period has a duration of 5 minutes to 90 days.

3. The method of claim 1, wherein said defined time period comprises a period of minutes or hours repeated over a period of days or weeks.

4. The method of claim 1, wherein said notification further comprises an audible, visual, or vibratory alarm.

5. The method of claim 1, wherein said graphical representation is displayed on an electronic monitoring unit.

6. The method of claim 1, wherein said graphical representation is displayed on a personal computer by the individual.

7. The method of claim 1, wherein said graphical representation is displayed on a computing device or on printed reports by a health professional.

8. The method of claim 1, wherein the integrated percentages of hyperglycemia, hypoglycemia, and normoglycemia are displayed using different font sizes and/or colors corresponding to the regions of the display and/or the displayed values.

9. The method of claim 1, wherein the integrated percentages of hyperglycemia, hypoglycemia, and normoglycemia are displayed in dynamic font sizes and wherein the font sizes are representative of relative values of the integrated percentages of hyperglycemia, hypoglycemia, and normoglycemia.

10. The method of claim 1, wherein the integrated percentage of normoglycemia is displayed as a number in a square, the integrated percentage of hyperglycemia is displayed as a number in an arrow pointing upward, and the integrated percentage of hypoglycemia is displayed as a number in an arrow pointing downward.

11. The method of claim 10, wherein the square and/or one or both of the arrows is colored.

12. The method of claim 10, wherein the square and the arrows are dynamically sized and wherein the sizes are representative of relative values of the integrated percentages of hyperglycemia, hypoglycemia, and normoglycemia.

13. The method of claim 1, wherein said notification further comprises a display of text indicating a condition of concern.

14. The method of claim 1, wherein said notification further comprises an indication of a relative level of concern based on the identified glucose level condition.

15. The method of claim 1, wherein said determining for the plurality of points of time over the defined time period the relative integrated percentages of hyperglycemia, hypoglycemia, and normoglycemia comprises determining the integrated areas for each region of hyperglycemia, hypoglycemia, and normoglycemia values over the defined time period and expressing those values as a percentage of the total area over the defined time period.

16. A method, comprising:
    receiving from a glucose sensing device a plurality of glucose values of an individual for a plurality of points of time over a defined time period;
    determining with an electronic monitoring unit for the defined period of time a hyperglycemia index value determined by summing a difference between a measured glucose value and a predefined hyperglycemia threshold for each of the plurality of points of time, if any, at which the measured glucose value is in excess of a predefined hyperglycemia threshold value to arrive at a hyperglycemia index value;

determining with the electronic monitoring unit for the defined period of time a hypoglycemia index value determined by summing a difference between a measured glucose value and a predefined hypoglycemia threshold for each of the plurality of points of time, if any, at which the measured glucose value is less than a predefined hypoglycemia threshold value to arrive at a hypoglycemia index value;

determining with the electronic monitoring unit for the defined period of time a normoglycemia index value determined by summing a difference between the measured glucose value and the closest threshold value, whether the closest threshold value is the predefined hyperglycemia threshold or the predefined hypoglycemia threshold, for each of the plurality of points of time, if any, at which a measured glucose value is within a predefined range of values between the predefined hyperglycemia threshold and the predefined hypoglycemia threshold to arrive at a normoglycemia index value; and displaying the hyperglycemia index value, the hypoglycemia index value, and the normoglycemia index value on an electronic monitoring unit associated with the glucose sensing device, wherein displaying comprises displaying a unified, graphical representation of the integrated percentages of hyperglycemia, hypoglycemia, and normoglycemia.

17. The method of claim 16, further comprising identifying a glucose level condition of the individual based on the hyperglycemia index value, the hypoglycemia index value, and the normoglycemia index value; and providing a notification of the glucose level condition to the individual.

18. An apparatus, comprising:

a glucose sensing device coupled to an electronic monitoring unit, said electronic monitoring unit comprising a storage medium and a plurality of programming instructions stored in the storage medium adapted to program the electronic monitoring unit to enable the electronic monitoring unit to:

receive a plurality of glucose values of an individual for a plurality of points of time over a defined time period;

determine for the plurality of points of time over the defined time period the relative integrated percentages of hyperglycemia, hypoglycemia, and normoglycemia;

identify a glucose level condition of the individual based on said relative integrated percentages of hyperglycemia, hypoglycemia, and normoglycemia; and provide a notification of the identified glucose level condition, wherein said notification comprises a display of a unified graphical representation of the integrated percentages of hyperglycemia, hypoglycemia, and normoglycemia.

* * * * *